United States Patent [19]

Sakurai et al.

[11] Patent Number: 5,042,460
[45] Date of Patent: Aug. 27, 1991

[54] ULTRASONIC TREATING APPARATUS WITH DEVICE FOR INHIBITING DRIVE WHEN ULTRASONIC ELEMENT IS DETERMINED TO BE DEFECTIVE

[75] Inventors: Tomohisa Sakurai, Hachioji; Masakazu Gotanda, Kanagawa; Toshihiko Suzuta, Hachioji; Tatsuya Kubota, Sagamihara; Kazuya Hijii, Hachioji; Yuichi Ikeda, Hachioji; Hitoshi Karasawa, Hachioji; Hiroaki Kagawa, Hachioji; Eiichi Fuse, Hachioji; Tetsumaru Kubota, Hachioji; Tadao Hagino, Yokohama, all of Japan

[73] Assignee: Olympus Optical Co., Ltd., Tokyo, Japan

[21] Appl. No.: 372,866

[22] Filed: Jun. 28, 1989

[30] Foreign Application Priority Data

Oct. 25, 1988 [JP]  Japan .............................. 63-138780[U]

[51] Int. Cl.⁵ ............................................. A61B 17/22
[52] U.S. Cl. ................................ 128/24 AA; 606/128; 310/316
[58] Field of Search ...................... 128/24 A; 604/22; 310/316; 606/128, 169, 170

[56] References Cited

U.S. PATENT DOCUMENTS

| 4,371,816 | 2/1983 | Wieser | 310/316 |
|---|---|---|---|
| 4,551,690 | 11/1985 | Quist | 310/316 |
| 4,658,172 | 4/1987 | Izukawa | 310/316 |
| 4,658,819 | 4/1987 | Harris et al. | 606/38 |
| 4,708,127 | 11/1987 | Abdelghani | 128/24 A |
| 4,721,107 | 1/1988 | Bolg et al. | 128/24 A |
| 4,791,915 | 12/1988 | Barsotti et al. | 128/24 A |
| 4,893,624 | 1/1990 | Lele | 128/24 A |
| 4,979,952 | 12/1990 | Kubota et al. | 128/24 AA |

FOREIGN PATENT DOCUMENTS

| 49-83398 | 8/1974 | Japan. |
|---|---|---|
| 50-40089 | 4/1975 | Japan. |
| WO87-01276 | 3/1987 | World Int. Prop. O. . |

Primary Examiner—Ruth S. Smith
Attorney, Agent, or Firm—Frishauf, Holtz, Goodman & Woodward

[57] ABSTRACT

An ultrasonic treating apparatus includes an inpedance detection unit for detecting the impedance of an ultrasonic vibration element for transmitting ultrasonic vibrations and a determining unit for determining whether the ultrasonic vibration element is good or not. If the ultrasonic vibration element is found not to be good, then a control unit inhibits ultrasonic vibrations from being generated from the ultrasonic vibration element. It is thus possible to prevent any breakage of the apparatus.

18 Claims, 11 Drawing Sheets

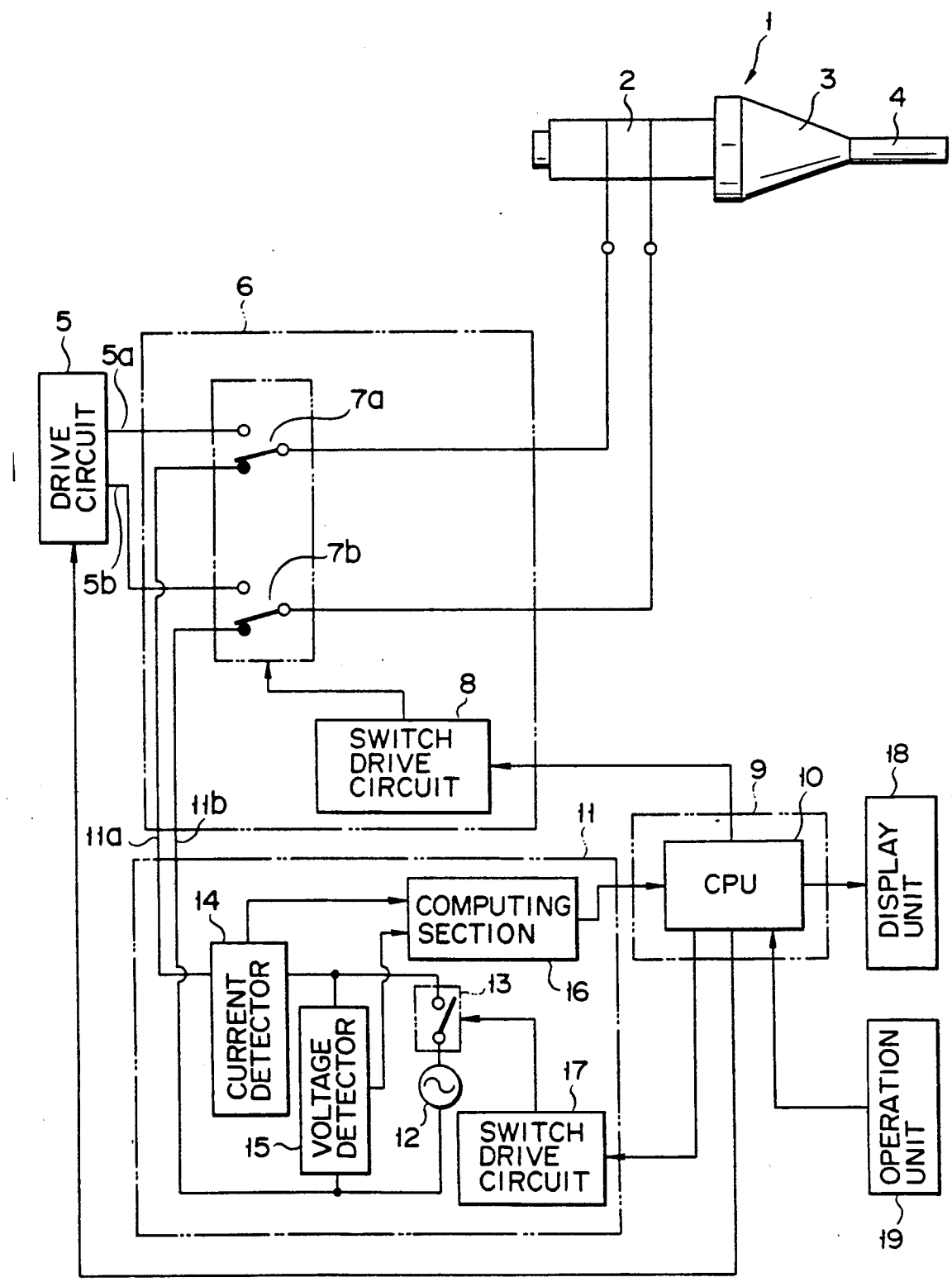
F I G. 1

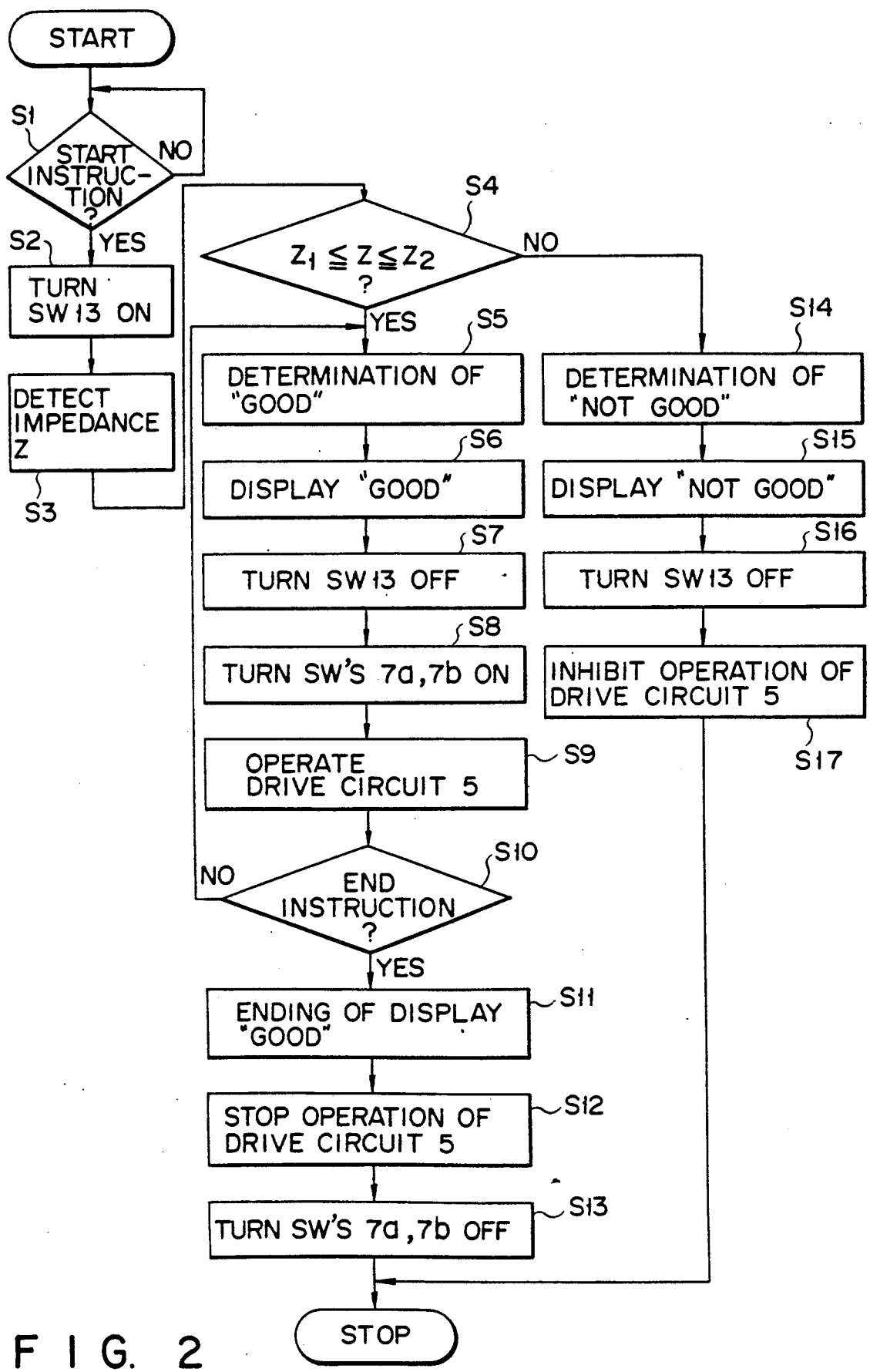
F I G. 2

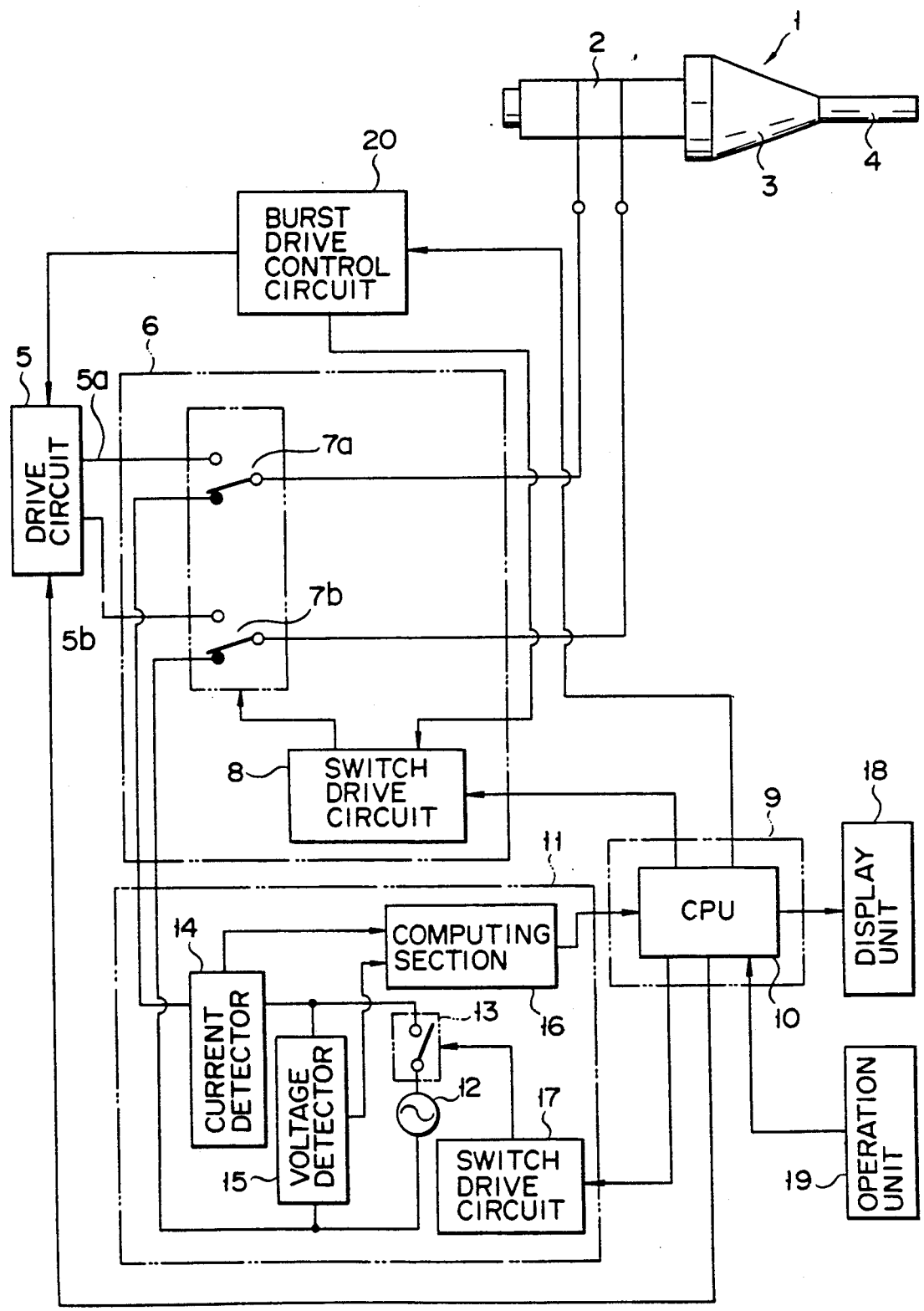
F I G. 3

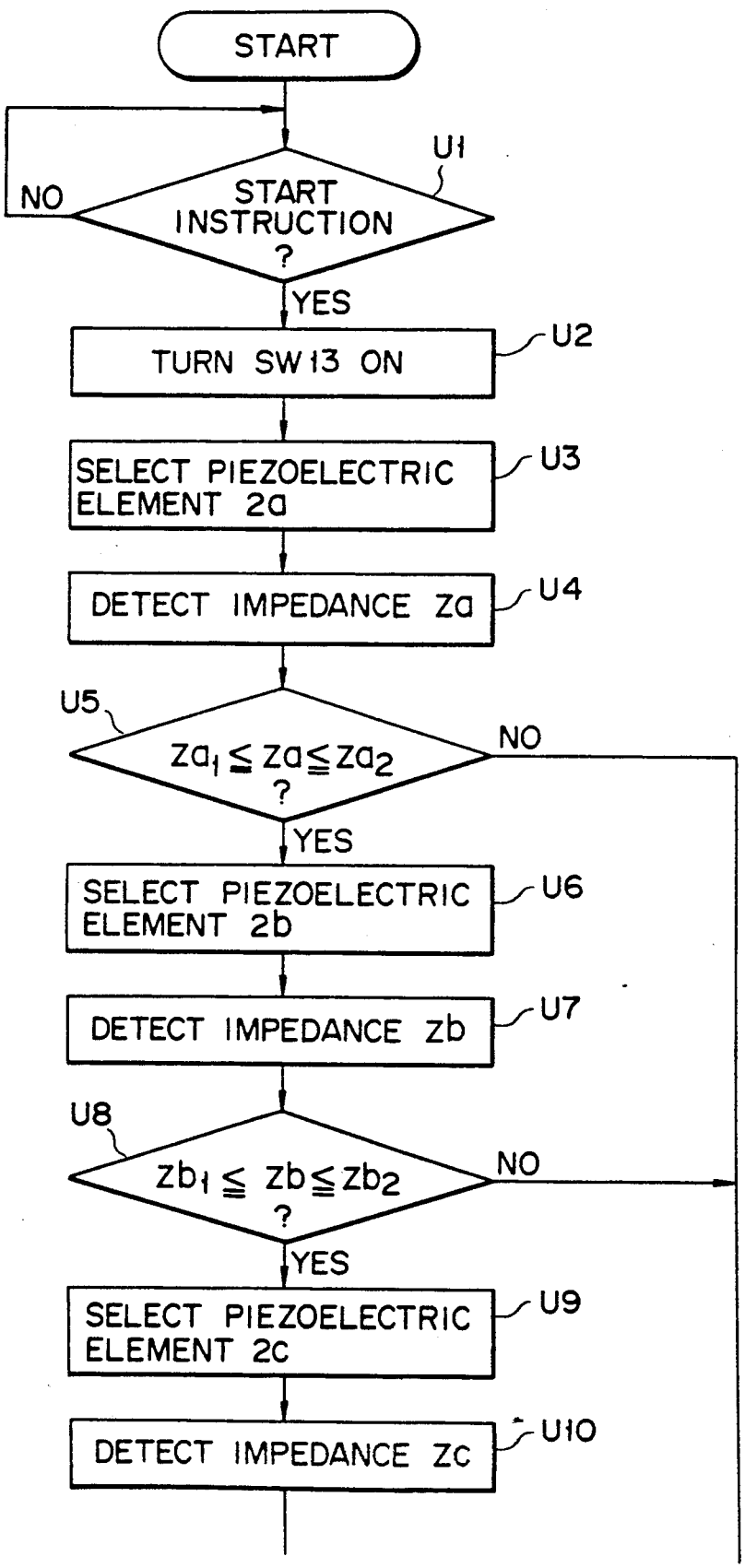
F I G. 6A

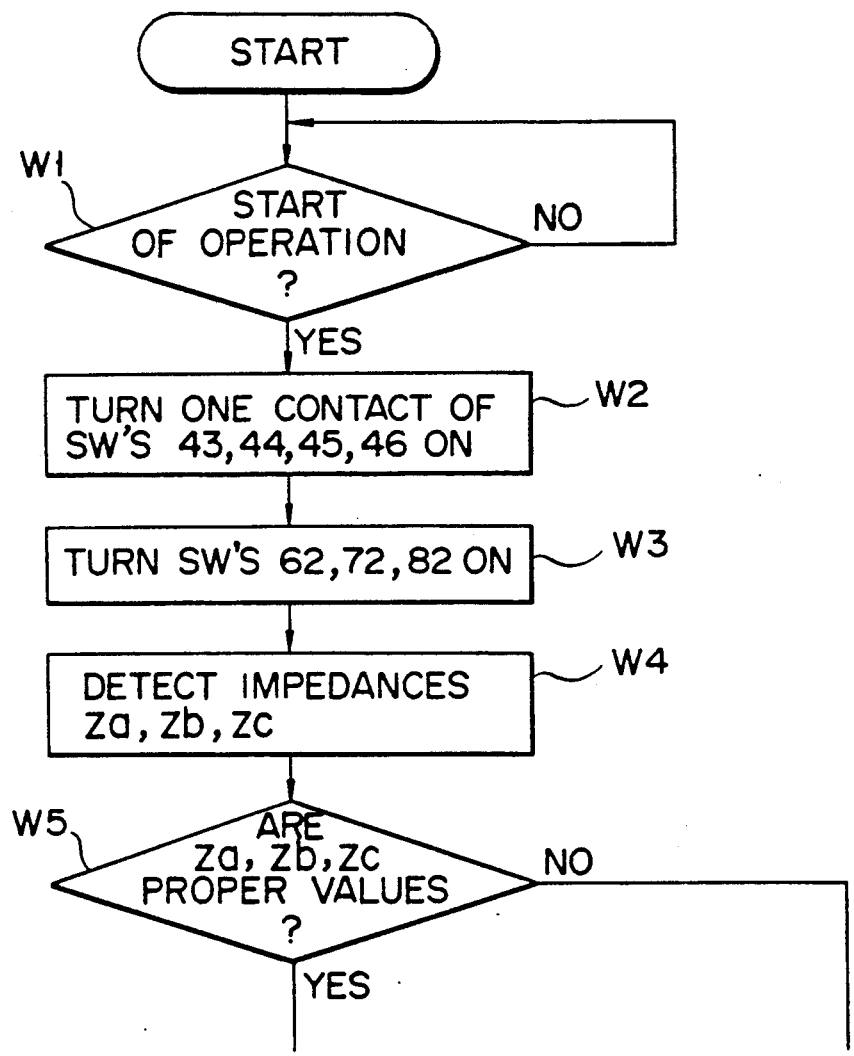
F I G. 8A

ULTRASONIC TREATING APPARATUS WITH DEVICE FOR INHIBITING DRIVE WHEN ULTRASONIC ELEMENT IS DETERMINED TO BE DEFECTIVE

BACKGROUND OF THE INVENTION

1. Field of the Invention

The present invention relates to an ultrasonic treating apparatus for resecting the prostate or destroying a calculus of a subject.

2. Description of the Related Art

It has so far been common practice to, upon the resecting of an affected living prostate, cauterize the prostate tissue with a high frequency current.

In recent times, an ultrasonic treating apparatus has increasingly been employed in that field of art.

The ultrasonic treating apparatus is adapted to cut an affected tissue of a subject with ultrasonic vibrations and includes an ultrasonic vibration element and a probe as an ultrasonic transmitter.

The probe of the ultrasonic treating apparatus is guided into the prostate of a living subject with an endoscope and the prostate can be resected with the ultrasonic vibrations with the probe being applied to that prostate site.

It is also possible for the ultrasonic treating apparatus to destroy the calculus of the subject.

In the above described ultrasonic treating apparatus, however, the ultrasonic vibration element sometimes fails and there is a risk of its being destroyed with a continuous use.

SUMMARY OF THE INVENTION

It is accordingly the object of the present invention to provide an ultrasonic treating apparatus which can avoid a risk of being damaged even when a defect occurs in the ultrasonic vibration element and assure added safety during use.

According to the present invention, there is provided an ultrasonic treating apparatus comprising an ultrasonic vibration element for transmitting ultrasonic vibrations to a region of interest of a subject, an impedance detection unit for detecting an impedance of the ultrasonic vibration element, a determining unit for determining whether the ultrasonic vibration element is good or not in accordance with the impedance which is detected by the impedance detecting unit, and a control unit which, when the ultrasonic vibration element is not good, inhibits the generation of the ultrasonic vibrations from the ultrasonic vibration element, in which, when the ultrasonic vibration element is not good, this state is detected by the impedance detection of the impedance detection unit and determination of the determining unit and the generation of the ultrasonic vibrations from the ultrasonic vibration element is inhibited by the operation of the control unit, thereby preventing the destruction, etc., of the apparatus per se.

In another embodiment of the present invention, there is provided an ultrasonic treating apparatus which comprises an ultrasonic vibration element for transmitting ultrasonic vibrations to a region of interest of a subject, a drive circuit for supplying an electric power to the ultrasonic vibration element for drive, a burst drive control unit for operating the drive circuit in ON-OFF fashion, an impedance detection unit for detecting the impedance of the ultrasonic vibration element, a determining unit for determining whether the ultrasonic vibration element is good or not in accordance with the impedance which is detected by the impedance detection unit and a control unit which, when the ultrasonic vibration element is not good, inhibits the operation of the drive circuit, in which, when the "not good" state occurs in the ultrasonic vibration element, it is detected by the impedance detection of the impedance detection unit and determination of the determining unit, whereby the operation of the drive circuit is inhibited by the control unit. By so doing, it is possible to inhibit the generation of ultrasonic vibrations from the ultrasonic vibration element and hence to prevent the destruction of the apparatus.

In still another embodiment of the present invention, there is provided an ultrasonic treating apparatus which comprises an ultrasonic vibration element including a plurality of layered piezoelectric elements and adapted to transmit ultrasonic vibrations to a region of interest of a subject, a drive circuit for supplying an electric power to the ultrasonic vibration element for drive, an impedance detection unit for detecting an impedance of respective piezoelectric elements, a determining unit for determining whether respective piezoelectric elements of the ultrasonic vibration element are good or not in accordance with the impedance which is detected by the impedance detection unit, and a control unit which, when a piezoelectric element is not good, inhibits the operation of the drive unit. In this embodiment, if any of the respective piezoelectric elements is defective, this state is detected by the impedance detection of the impedance detection unit and determination of the determining unit and the operation of the drive circuit is inhibited by the operation of the control unit. It is, therefore, possible to inhibit the generation of the ultrasonic vibration from the ultrasonic vibration element and to prevent the destruction of the apparatus.

BRIEF DESCRIPTION OF THE DRAWINGS

FIG. 1 is a circuit diagram showing an ultrasonic treating apparatus according to a first embodiment of the present invention;

FIG. 2 is a flowchart for explaining the operation of the embodiment shown in FIG. 1;

FIG. 3 is a circuit diagram showing an ultrasonic treating apparatus according to a second embodiment of the present invention;

FIGS. 6A and 6B form a flowchart for explaining the operation of the embodiment shown in FIG. 5;

FIGS. 8A and 8B form a flowchart for explaining the operation of the embodiment shown in FIG. 7.

DETAILED DESCRIPTION OF THE PREFERRED EMBODIMENTS

Figure 4A:
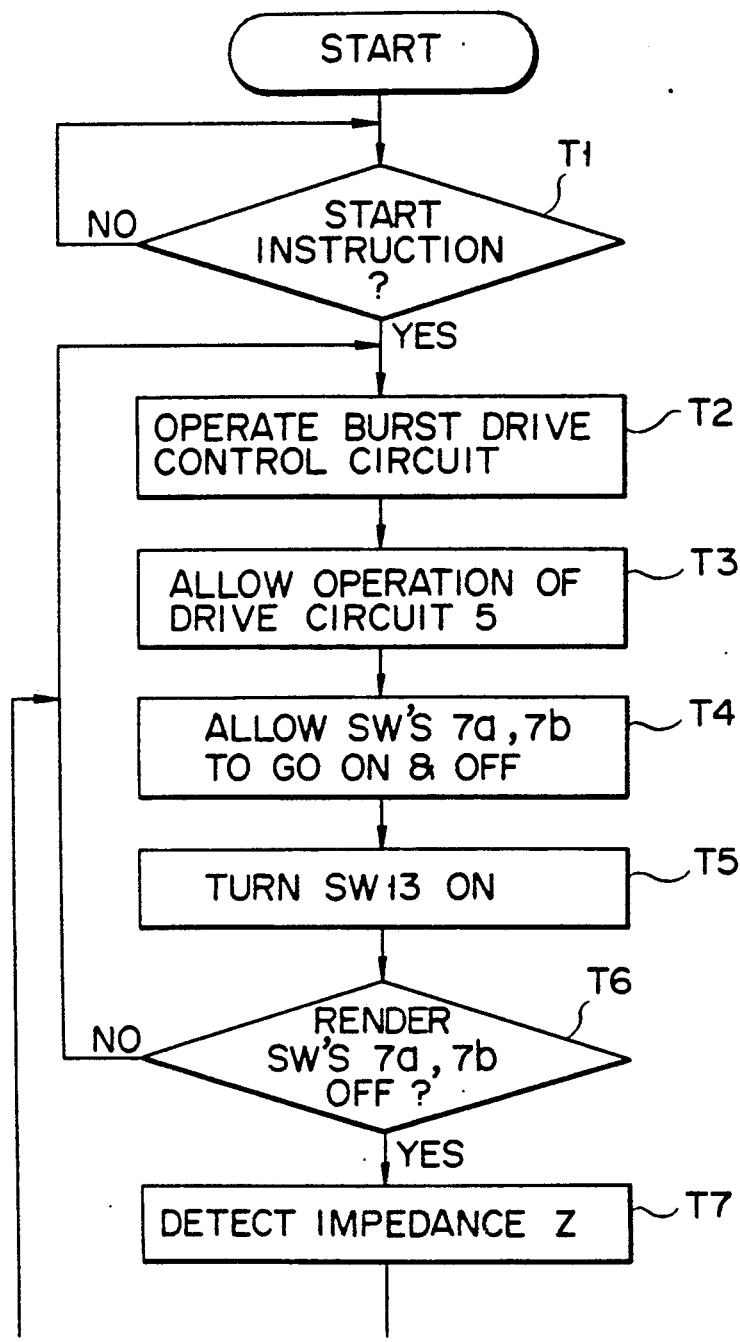
FIGS. 4A and 4B form a flowchart for explaining the operation of the embodiment shown in FIG. 3.

A first embodiment of the present invention will be explained below in conjunction with FIGS. 1 and 2.

In FIG. 1, a forward tip 1 of a handpiece comprises an ultrasonic vibration element 2, horn 3 and probe 4.

The ultrasonic vibration element 2 transmits ultrasonic vibrations onto a region of interest (ROI) of a subject. The ultrasonic vibrations which are transmitted from the ultrasonic vibration element 2 are amplified by the horn 3 and transmitted to the probe 4.

The probe 4 is formed of a transmitting element for transmitting the ultrasonic vibrations to the ROI of the subject and adapted to be guided there with the use of, for example, an endoscope.

A drive circuit 5 is operated in accordance with an instruction of a CPU 10 as will be set forth in more detail below and a driving electric power is applied across output terminals 5a and 5b so that the ultrasonic vibration element may be driven.

The output terminal 5a of the drive circuit 5 is connected to one terminal of the ultrasonic vibration element 2 via a normally open contact of a switch 7a.

The output terminal 5b of the drive circuit 5 is connected to the other terminal of the ultrasonic vibration element 2 via a normally open contact of a switch 7b in a changeover circuit 6.

The changeover circuit 6 comprises of the switches 7a, 7b and a switch drive circuit 8. The switch drive circuit 8 drives the switches 7a, 7b in accordance with an instruction of a CPU (central processing unit) 10 in a good/not good determining circuit 9.

One end of the ultrasonic vibration element is connected to an output terminal 11a of an impedance detection circuit 11 via the normally closed contact of the switch 7a.

The other end of the ultrasonic vibration element 2 is connected to an output terminal 11b of the impedance detection circuit 11 via the normally closed contact of the switch 7b.

The impedance detection circuit 11 comprises the output terminals 11a, 11b, an AC power source 12 for supplying an AC voltage to the output terminals 11a, 11b, a switch 13 provided on a current conduction path between the AC power source 12 and the output terminals 11a, 11b, a current detector 14, a current detector 14 provided between the AC power source 12 and the output terminals 11a, 11b, a voltage detector 15 connected to the AC power source 12 via the switch 13, a computing section 16 for computing an impedance of the ultrasonic vibration element 2 on the basis of a detection voltage of the voltage detector 15 and current detector 14, and a switch drive circuit 17 for driving the switch 13.

Here, the computing section 16 divides a detection voltage V of the voltage detection 15 by a detection current I of the current detection 14 to find an impedance Z of the ultrasonic vibration element 2. The impedance Z thus found is sent to a CPU 10 in the good/not good determining circuit 9.

The switch drive circuit 17 drives the switch 13 in accordance with an instruction of the CPU 10.

The good/not good determining circuit 9 is mainly constructed of the CPU 10 and determines the good/not good state of the ultrasonic vibration element 2 in accordance with the impedance Z which is detected in the impedance detection circuit 11.

The drive circuit 5, switch drive circuit 8, computing section 16, switch drive circuit 17, display unit 18 and operating unit 19 are connected to the CPU 10.

The display unit 18 displays, for example, a result of determination by the CPU 10. The operation unit 19 gives an instruction to start and end the treating operation on the ROI of the subject to be treated.

The CPU 10 has, means for determining the good/not good state of the ultrasonic vibration element 2, a control function means for controlling the drive circuit 5, switch drive circuit 8 and switch drive circuit 17 in accordance with the instructions and so on of the operation unit 19 and control function means for inhibiting the generation of the ultrasonic vibrations by the ultrasonic vibration element 2 when the good/not good state is determined in the good/not good state determining circuit.

The function of the ultrasonic treating apparatus thus constructed will be explained below in more detail by referring to FIG. 2.

Suppose that the operation unit 19 outputs a start-to-treat instruction at step S1. In this case, the CPU 10 issues an instruction to the switch drive circuit 17 in the impedance detection circuit 11 to turn the switch 13 ON (step S2).

With the switch 13 turned ON, a voltage on the AC power source 12 is created across the output terminals 11a, 11b via the current detector 14. The voltage is applied to the ultrasonic vibration element 2 via the normally closed contacts of the switches 7a, 7b in the changeover circuit 6.

As a result, a current I flows through the ultrasonic vibration element 2 and detected by the current detector 14. The result of detection is sent to the computing section 16.

With the switch 13 turned ON, a voltage V on the AC power source 12 is detected by the voltage detector 15 and a result of detection is sent to the computing section 16.

The computing section 16 divides the voltage V by the current I to find an impedance Z of the ultrasonic vibration element 2 at step S3. The impedance Z thus found is fed to the CPU 10.

The CPU 10 ascertains whether the impedance Z is within a predetermined range, such as $Z_1 \leq Z \leq Z_2$, at step S4. Here $Z_1$ and $Z_2$ denote the setting values. If the impedance Z is a proper value, the CPU 10 determines that the ultrasonic vibration element 2 is good at step 5.

If the CPU 10 determines that the ultrasonic vibration element 2 is good, then the display 18 indicates "good" at step S6. The switch 13 is turned OFF, stopping the operation of the impedance detection circuit 11 (step 7). The CPU 10 turns the switches 7a, 7b ON, connecting the ultrasonic vibration element 2 to the drive circuit 5 (step S8). Then the drive circuit 5 is operated at step S9.

A drive circuit 5 delivers a drive electric power from the drive circuit 5 to the ultrasonic vibration element 2 via the normally open contacts of the switches 7a, 7b. By doing so, the ultrasonic vibration element 2 is driven to generate ultrasonic vibrations from the ultrasonic vibration element 2.

At the time of transmitting the ultrasonic vibrations, it is assumed that an instruction for ending the treating procedure is given by the operation unit 19 (step S10).

At this time, the CPU 10 ends a display "good" on the display unit 18 at step S11. Further, the CPU 10 stops the operation of the drive circuit 5 at step S12 and the switches 7a, 7b are turned OFF at step S13. As a result, the driving operation of the ultrasonic vibration element 2 is ended, thus ending the generation of the ultrasonic vibrations from the ultrasonic vibration element 2.

In step S4, if the impedance Z is not within the range of $Z_1 \leq Z \leq Z_2$, that is, within a proper value range, the CPU 10 determines that the ultrasonic vibration element 2 is not good (step S14).

If the CPU 10 makes such a determination, then the display unit 18 displays "not good" at step S15. The switch 13 is turned OFF, stopping the operation of the impedance detection circuit 11 (step S16). The CPU 10 inhibits the operation of the drive circuit 5 in spite of an instruction of the operation unit 19 (step S17).

In this case, the ultrasonic vibration element 2 is not driven and ultrasonic vibrations are not generated from the ultrasonic vibration element 2. It is thus possible to avoid a risk of the apparatus being destroyed, for example, thus obtaining an added safety.

Since the "not good" is displayed on the display unit 18, the user immediately knows that the lack of ultrasonic vibrations is caused by the "not good" state of the ultrasonic vibration element 2. Thus the user can operate the apparatus with added safety.

Figure 4B:
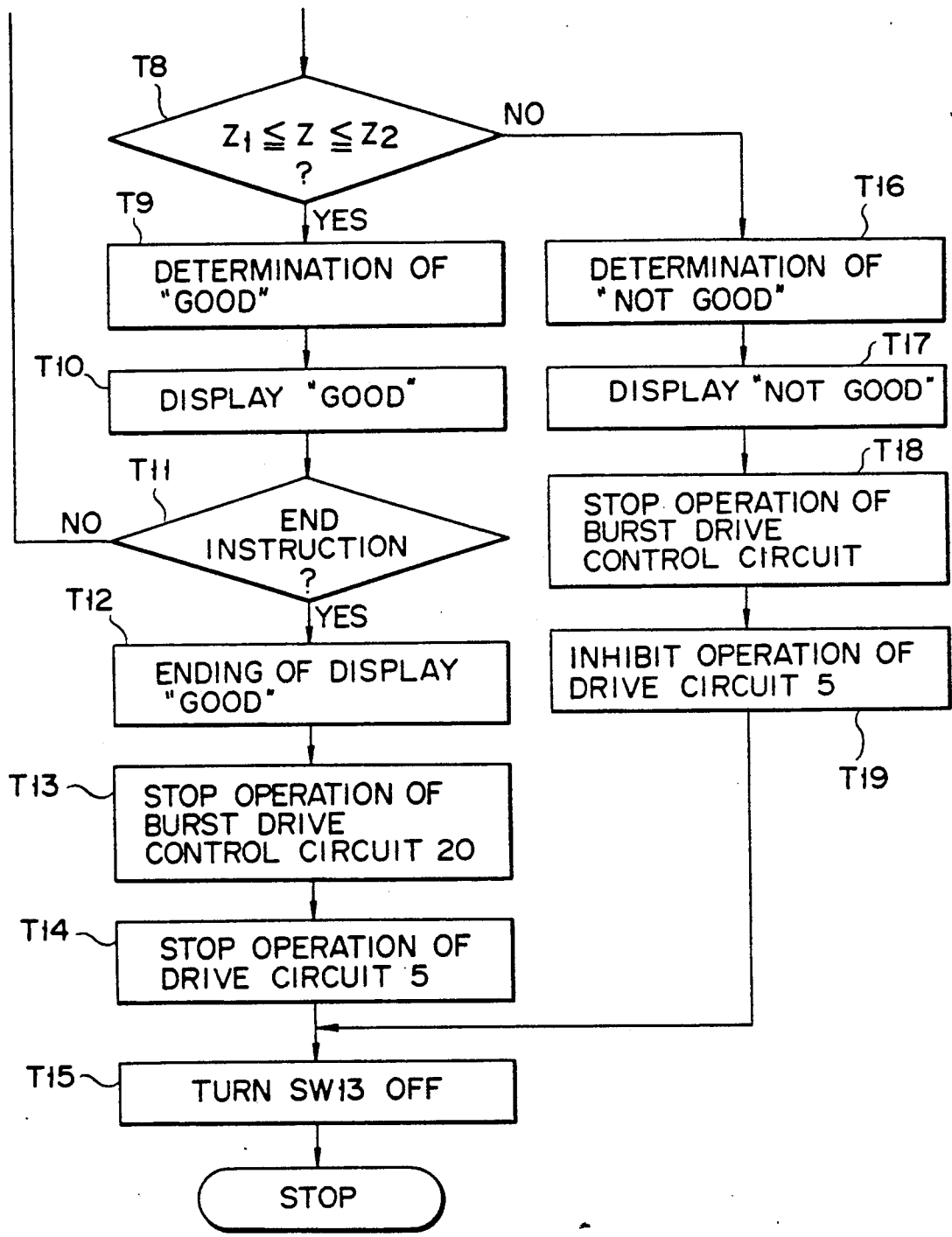

A second embodiment of the present invention will be explained below with reference to FIGS. 3, 4A and 4B. In FIG. 3, the same reference numerals are employed to designate parts or elements corresponding to those shown in FIG. 1. Further explanation is thus omitted.

In the embodiment, a burst drive control circuit 20 is connected to a CPU 10 and adapted to operate a drive circuit 5 in ON-OFF fashion.

The burst drive control circuit 20 has the function of outputting a signal representing a burst drive control state. This signal is supplied to a switch drive circuit 8 in a changeover circuit 6.

The CPU 10 has a function means for determining the good/not good state of the ultrasonic vibration element 2 in accordance with an impedance Z detected at an impedance detection circuit 11, a function means for controlling a drive circuit 5, switch drive circuit 8, switch drive circuit 17 and burst drive control circuit 20 and a control function means for inhibiting the generation of ultrasonic vibrations by an ultrasonic vibration element 2 when a "not good" state is determined by the determining function means.

The function of the ultrasonic treating apparatus will be explained below by referring to FIGS. 4A and 4B.

Assume that a start-to-treat instruction is issued from an operation unit 19 (step T1). Then the CPU 10 operates a burst drive control circuit 20 at step T2. The CPU 10 allows the operation of the drive circuit 5 at step T3 and then allows switches 7a, 7b to be turned ON and OFF by the switch drive circuit 8 at step T4.

Thus the drive circuit 5 is turned ON and OFF and the switches 7a, 7b are turned ON in accordance with the ON operation of the drive circuit 5.

That is, a drive electric power is supplied from the drive circuit 5 to the ultrasonic vibration element 2 via normally open contacts of switches the burst drive of the ultrasonic vibration element 2.

The CPU 10 supplies an instruction to the switch drive circuit 17, turning a switch 13 ON (step T5).

With the switch 13 ON, a voltage on an AC power source 12 emerges between output terminals 11a and 11b via a current detector 14. With the switches 7a, 7b OFF, that voltage is applied to the ultrasonic vibration element 2 via normally closed contacts of the switches 7a, 7b.

The switches 7a, 7b are turned OFF at step T6 and a current I flows through the ultrasonic vibration element 2. On the other hand, the current I is detected by the current detector 14 and, at the same time, a voltage V on the AC power source 12 is detected by the voltage detector 15. A computing section 16 divides the voltage V by the current I to find an impedance Z of the ultrasonic vibration element 2 (step T7).

The CPU 10 ascertains whether or not the impedance Z falls within a predetermined impedance range, for example, within a range of $Z_1 \leq Z \leq Z_2$ ($Z_1$ and $Z_2$: the setting values) at step T8. If, here, the impedance Z is any proper value, the CPU 10 determines that the ultrasonic vibration element 2 is good (step T9).

If the "good" state is so determined by the CPU 10 a display "good" is made on a display unit 18 at step T10. The burst drive operation and impedance detection continue whereby ultrasonic vibrations are generated from the ultrasonic vibration element 2.

It is assumed that, at the time of the generation of the ultrasonic vibrations, a treatment procedure ending instruction is issued from the operation unit 19 (step T11).

By the CPU 10, the display "good" is ended on the display unit 18 (step T12). Then the CPU 10 stops the operation of the burst drive control circuit 20 at step T13 and then that of the drive circuit 5 at step T14. The switch 13 is turned OFF at step T15, stopping the operation of the impedance detector 11. When this occurs, the burst drive operation of the ultrasonic vibration element 2, as well as the detection of the impedance, is ended, so that the generation of the ultrasonic vibrations by the ultrasonic vibration element 2 is terminated.

If, at step T8, the impedance Z does not fall within a proper value range, that is, within a range of $Z_1 \leq Z \leq Z_2$ ($Z_1$ and $Z_2$ the setting values), the CPU 10 determines that a defect occurs in the ultrasonic vibration element 2 at a step T16.

If the presence of such a defect is determined by the CPU 10, the display "not good" is made on the display unit 18 at step T17 and the operation of the burst drive control circuit 20 is stopped at step T18. The CPU 10 inhibits the operation of the drive control circuit 5 in spite of an instruction from the operation unit 19 (step T19) and, at the same time, the switch 13 is turned OFF, stopping the operation of the impedance detector 11 (step T15).

In this case, the burst drive of the ultrasonic vibration element 2 is immediately stopped, immediately stopping the generation of the ultrasonic vibrations from the ultrasonic vibration element 2. It is thus possible to avoid a risk of destruction, etc., of the apparatus and to ensure added safety to the user.

Since the display "not good" is made on the display unit 18, the user immediately finds the ultrasonic vibration element 2 defective and hence the absence of ultrasonic vibrations. It is thus possible to offer added safety to the user.

Figure 5:
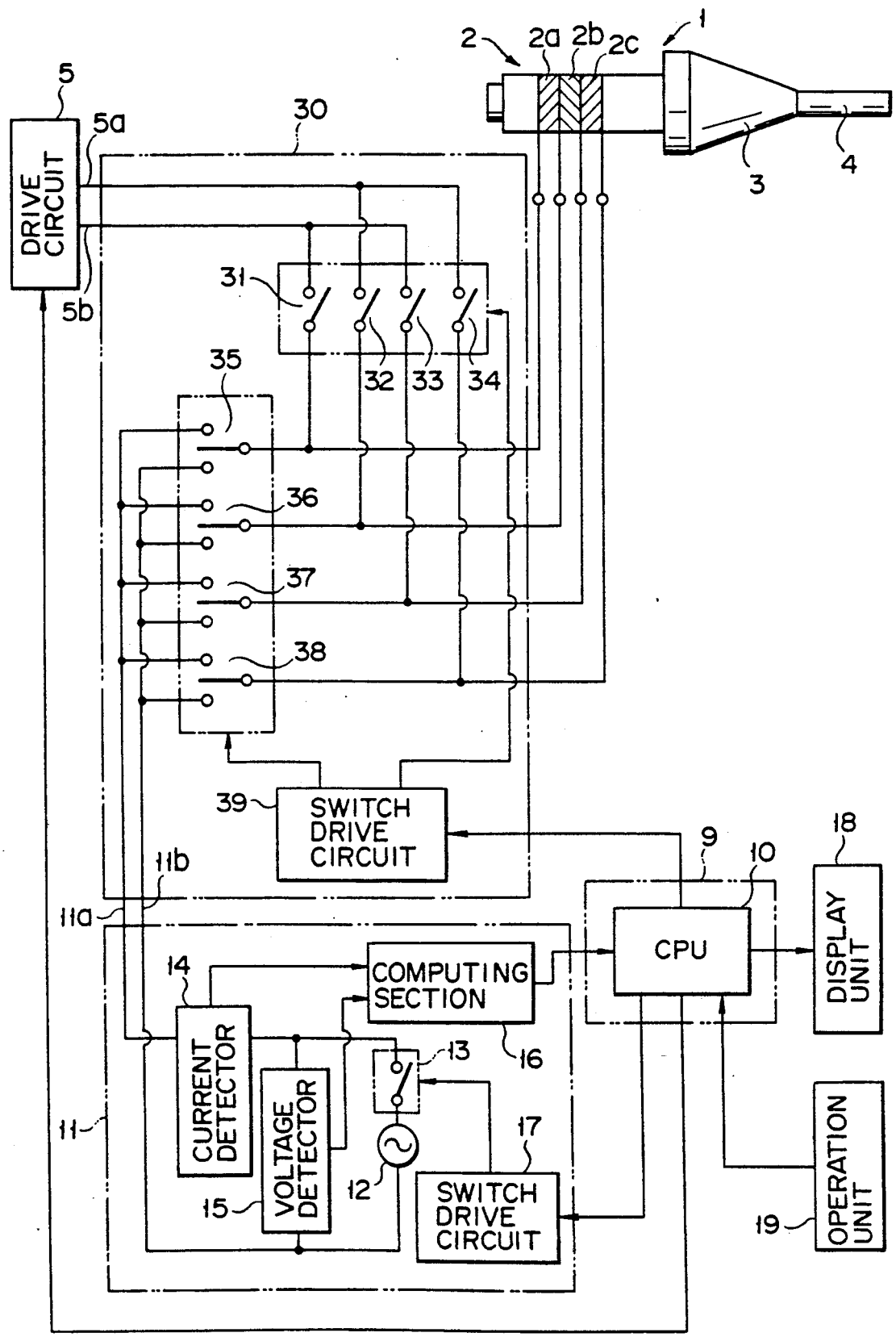
FIG. 5 is a circuit diagram showing an ultrasonic treating apparatus according to a third embodiment of the present invention.
Figure 6B:
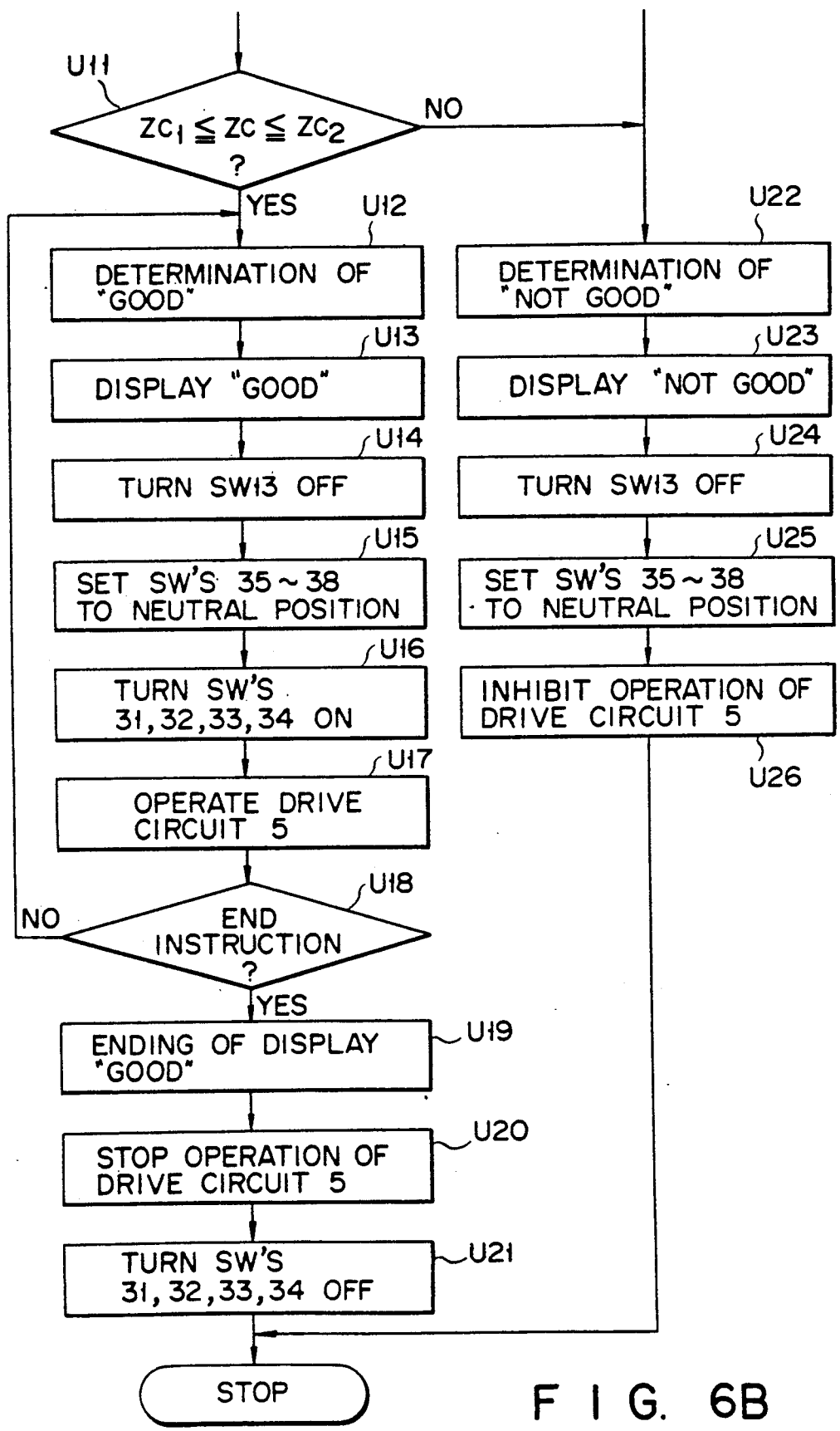

A third embodiment of the present invention will now be explained below by referring to FIGS. 5, 6A and 6B. In FIG. 5, the same reference numerals are employed to designate parts and elements corresponding to those shown in FIGS. 1 and 3. Any further explanation is therefore omitted.

In this embodiment, an impedance is detected for a plurality of piezoelectric elements 2a, 2b, 2c which constitute essential elements of an ultrasonic vibration element 2.

As shown in FIG. 5, the ultrasonic vibration element 2 comprises a plurality of layered piezoelectric elements 2a, 2b, 2c.

On end of the piezoelectric element 2a is connected to an output terminal 5b of a drive circuit 5 via a switch 31 in a changeover circuit 30. The other end of the piezoelectric element 2a is connected to an output terminal 5a of the drive circuit 5 via a switch 32 in the changeover circuit 30. One end of the piezoelectric element 2b is connected via the switch 32 to the output terminal 5 of the drive circuit 5. The other end of the piezoelectric element 2b is connected to the output terminal 5b of the drive circuit 5 via a switch 33 in the changeover circuit 30.

One end of the piezoelectric element 2C is connected to the output terminal 5b of the drive circuit 5 via the aforementioned switch 33. The other end of the piezoelectric element 2c is connected to the output terminal 5a of the drive circuit 5 via a switch 34 in the changeover circuit 30.

The changeover circuit 30 comprises the switches 31, 32, 33, 34, switches 35, 36, 37, 38 and switch drive circuit 39. The switch drive circuit 39 drives the switches 31, 32, 33, 34, 35, 36, 37 and 38 in accordance with an instruction of the CPU 10.

The switches 35, 36, 37, 38 are of a two-way type having a neutral position.

One end of the piezoelectric element 2a is connected to an output terminal 11a of an impedance detection circuit 11 via one contact of the switch 35. The other end of the piezoelectric element 2a is connected to an output terminal 11b of the impedance detector 11 via the other contact of the switch 36.

One end of the piezoelectric element 2b is connected to the output terminal 11a of the impedance detection circuit 11 via one contact of the switch 36. The other end of the piezoelectric element 2b is connected to the output terminal 11b of the impedance detection circuit 11 via the other contact of the switch 37.

One end of the piezoelectric element 2c is connected to the output terminal 11a of the impedance detection circuit 11 via one contact of the switch 37. The other terminal of the piezoelectric element 2c is connected to the output terminal 11b of the impedance detection circuit 11 via the other contact of the switch 38.

The drive circuit 5, computing section 16, switch drive circuit 17, display unit 18, operation unit 19 and switch drive circuit 39 are connected to a CPU 10.

The CPU 10 has a function means for determining whether each piezoelectric element of the ultrasonic vibration element 2 is good or not in accordance with an impedance detected by the impedance detection circuit, function means for controlling the drive circuit 5, switch drive circuit 17 and switch drive circuit 39 in accordance with, for example, an instruction of the operation unit 19, and control means for inhibiting the generation of ultrasonic vibrations from the ultrasonic vibration element 2 when a piezoelectric element is found defective.

The operation of the ultrasonic treating apparatus will be explained below with reference to FIGS. 6A and 6B.

Now suppose that a start-to-treat instruction is issued from the operation unit 19 (step U1). The CPU 10 supplies an instruction to the switch drive circuit 17 in the impedance detection circuit 11, turning the switch 13 ON (step U2).

With the switch 13 ON, a voltage on the AC power source 12 is created across the output terminals 11a and 11b via the current detector 14.

The CPU 10 supplies an instruction to the switch drive circuit 39 in the changeover circuit 30, turning one contact of the switch 35 ON and the other contact of the switch 36 ON in which case the switches 37 and 38 are set to a neutral position. That is, the piezoelectric element 2, of the ultrasonic vibration element 2 is connected to the output terminals 11a and 11b of the impedance detection circuit 11 at step U3.

A voltage which is developed between the output terminals 11a and 11b is applied to the piezoelectric element 2a via the switches 35 and 36. As a result, a current I flows through the piezoelectric element 2a and is detected by the current detector 14. A result of detection is supplied to the computing section 16.

With the switch 13 ON, a voltage V on the AC power supply 12 is detected by the voltage detector 15. A result of detection is fed to the computing section 16.

The computing section 16 divides the voltage V by the current I and finds an impedance $Z_a$ at step U4. The impedance $Z_a$ thus found is sent to the CPU 10.

The CPU 10 ascertains whether or not the impedance $Z_a$ falls within a predetermined impedance range, for example, is a proper value of $Z_{a1} \leq Z_a \leq Z_{a2}$ range ($Z_{a1}$, $Z_{a2}$ the setting values)-step U5.

If, at the ascertaining step, the impedance $Z_a$ is found to be a proper value, then the piezoelectric element 2b is next selected.

That is, the CPU 10 turns one contact of the switch 36 ON and the other contact of the switch 37 ON in which case the switches 35, 38 are set to a neutral position. Thus the piezoelectric element 2b of the ultrasonic vibration element 2 is connected to the output terminals 11a, 11b (step U6).

A voltage which is developed across the output terminals 11a and 11b is applied to the piezoelectric element 2b via the switches 36 and 37. At this time, a current I flows through the piezoelectric element 2b and the computing section 16 finds an impedance $Z_b$ of the piezoelectric element 2b at step U7. The impedance $Z_b$ thus found is sent to the CPU 10.

The CPU 10 ascertains whether or not the impedance $Z_b$ falls within a predetermined range, for example, within a $Z_{b1} \leq Z_b \leq Z_{b2}$ range ($Z_{b1}$, $Z_{b2}$ the setting values) at step U8.

It, at this ascertaining step, the impedance $Z_b$ is a proper value, then the piezoelectric element $2_c$ is next selected.

The CPU 10 turns one contact of the switch 37 ON and the other contact of the switch 38 ON. At this time, the switches 35 and 36 are set to the neutral position. That is, the piezoelectric element $2_c$ of the ultrasonic vibration element 2 is connected to the output terminals 11a and 11b at step U9.

A voltage which is induced between the output terminals 11a and 11b is applied to the piezoelectric element 2c via the switches 37 and 38. In consequence, a current I flows through the piezoelectric element 2c and the impedance $Z_c$ of the piezoelectric element 2c is found by the computing section 16 (at step U10). The impedance $Z_c$ thus found is fed to the CPU 10.

The CPU 10 ascertians whether or not the impedance $Z_c$ falls within a predetermined impedance range, for example, within a $Z_{c1} \leq Z_c \leq Z_{c2}$ range ($Z_{c1}$, $Z_{c2}$: the setting values)-step U11.

If, at the ascertaining step, the impedance $Z_c$ is a proper value, the CPU 10 determines that the piezoelectric elements 2a, 2b, 2c are good (step U12).

If the CPU 10 determines a piezoelectric element as being "good", the display "good" is made on the display unit 18 at step U13.

The switch 13 is turned OFF, stopping the operation of the impedance detection circuit 11 at step U14. The CPU 10 sets the switches 35, 36, 37, 38 to the neutral position at step U15 and the switches 31, 32, 33, 34 are turned ON at step U16.

Upon the setting of the switches 35, 36, 37, 38 to the neutral position, the piezoelectric elements 2a, 2b, 2c are separated from the impedance detection circuit 11.

With the switches 31, 32, 33 and 34 ON, the piezoelectric elements 2a, 2b, 2c are connected to the drive circuit 5.

In that state, the CPU 10 operates the drive circuit 5 at step U17.

Thus a drive electric power is supplied from the drive circuit 5 to the piezoelectric elements 2a, 2b, 2c via the switches 31, 32, 33, 34. As a result, the ultrasonic vibration element 2 is driven and ultrasonic vibrations are transmitted from the ultrasonic vibration element 2.

In the transmission of the ultrasonic vibrations as set forth above, it is assumed that an instruction for ending a treatment procedure is issued from the operation unit 19 at step U18.

At this time, the CPU 10 eliminates the display "good" from the surface of the display 18 at step U19. The CPU 10 stops the operation of the drive circuit 5 at step U20 and the switches 31, 32, 33, 34 are turned OFF at step U21. When this occurs, the drive operation of the ultrasonic vibration element 2 is terminated, stopping the transmitting of the ultrasonic vibrations from the ultrasonic vibration element 2.

At the ascertaining step U5, if the impedance $Z_a$ is not within the predetermined range, the CPU 10 determines the piezoelectric element 2a as being defective at step U22.

At the ascertaining step U8, if the impedance $Z_b$ is not within the predetermined range, that is, is not a proper value, the CPU 10 determines the piezoelectric element 2b as being defective at step U22.

At the ascertaining step U11, if the impedance $Z_c$ is not within the predetermined value range, the CPU 10 determines the piezoelectric element 2c as being defective at step U22.

When the CPU 10 determines that even one of the piezoelectric elements 2a, 2b and 2c is not good, then the display "not good" is displayed on the surface of the display 18 at step U23. The switch 13 is turned OFF, stopping the operation of the impedance detection circuit 11 at step U24. The CPU 10 sets the switches 35, 36, 37, 38 to the neutral position at step U25, inhibiting the operation of the drive circuit 5 in spite of an instruction from the operation unit 19 (step U26).

In this case, the ultrasonic vibration element 2 is not driven and hence the ultrasonic vibration element 2 generates no ultrasonic vibrations. There is, therefore, no risk that the present apparatus will be destroyed. The user can operate the apparatus safely.

From the display "not good" made on the surface of the display unit 18, the user can immediately know that the absence of ultrasonic vibrations is caused by the defect of the ultrasonic vibration element 2. Thus the user can use the apparatus with adequate reliability.

Figure 7:
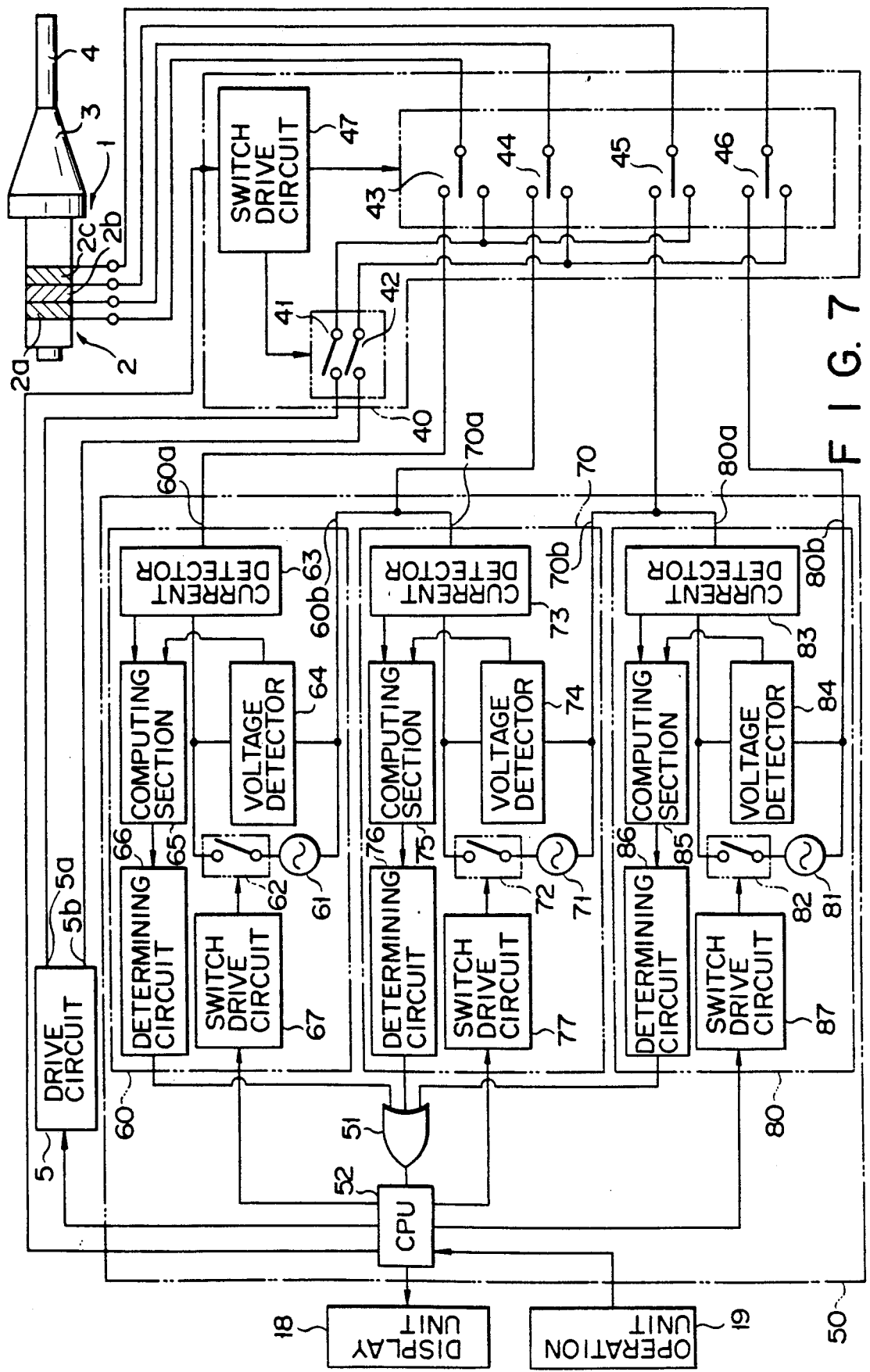
FIG. 7 is a circuit diagram showing an ultrasonic treating apparatus according to a fourth embodiment of the present invention.
Figure 8B:
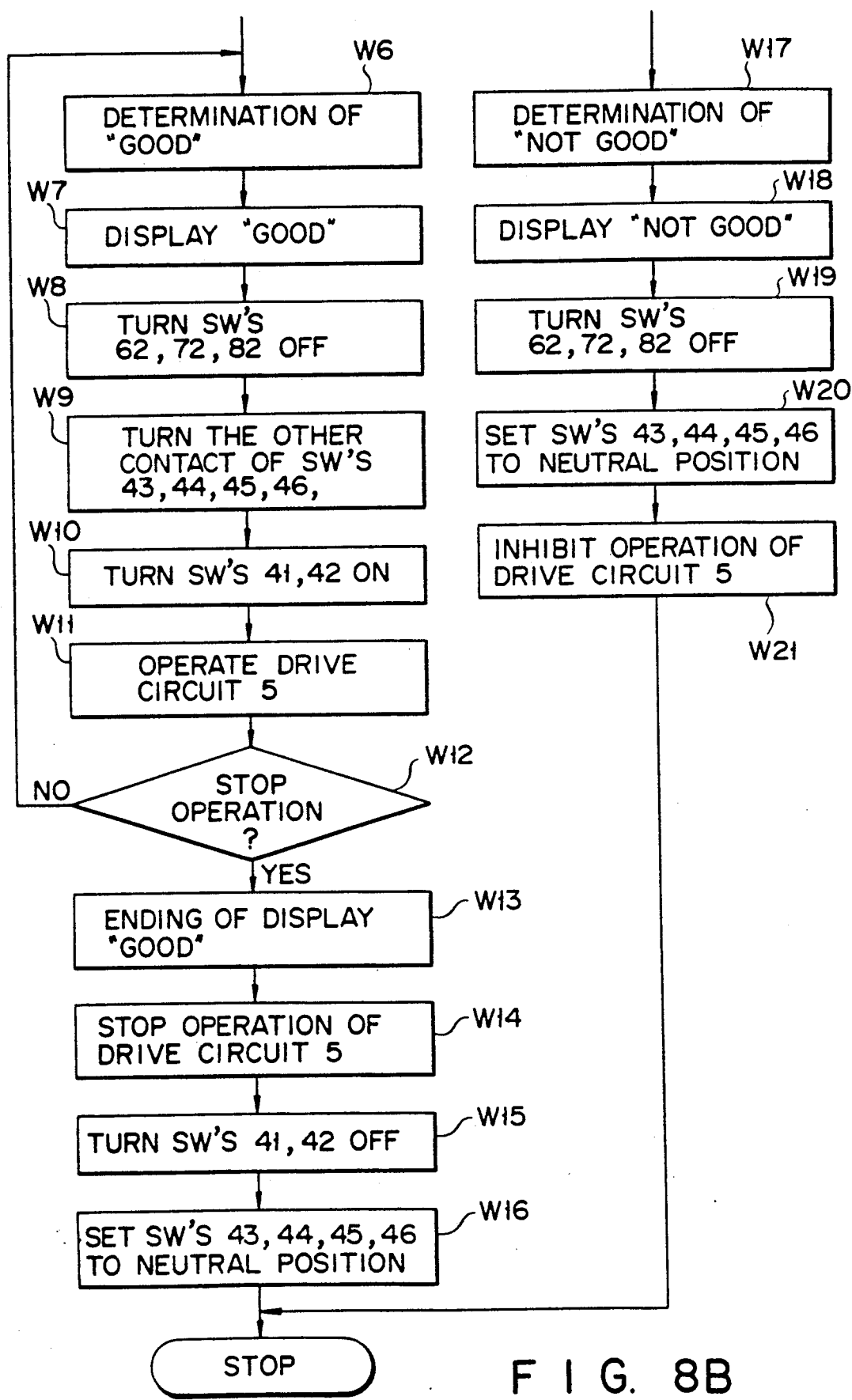

The fourth embodiment of the present invention will now be described below by referring to FIGS. 7, 8A and 8B. In FIG. 7, the same reference numerals are employed to designate parts or elements corresponding to those shown in FIGS. 1, 3 and 5. Further explanation is therefore omitted.

In this embodiment, an impedance is simultaneously detected for a plurality of piezoelectric elements 2a, 2b, 2c which comprise an ultrasonic vibration element 2.

One end of the piezoelectric element 2a is connected to an output terminal 5a of a drive circuit 5 via the other contact of a switch 43 and switch 41 in a changeover circuit 40. The other end of the piezoelectric element 2a is connected to an output terminal 5b of the drive circuit 5 via the other contact of a switch 44 and switch 42 in the changeover circuit 40.

One end of the piezoelectric element 2b is connected to an output terminal 5b of the drive circuit 5 via the other end of the switch 44 and switch 42 in the changeover switch 40. The other end of the piezoelectric element 2b is connected to the output terminal 5a of the drive circuit 5 via the other contact of the switch 45 and switch 41 in the changeover circuit 40.

One end of the piezoelectric element 2c is connected to the output terminal 5a of the drive circuit 5 via the other contact of the switch 45 and switch 41 in the changeover circuit 40. The other end of the piezoelectric element 2c is connected to the output terminal 5b of the drive circuit 5 via the other contact of the switch 46 and switch 42 in the changeover circuit 40.

The changeover circuit 40 comprises the switches 41, 42, switches 43, 44, 45, 46 and switch drive circuit 47. The switch drive circuit 47 drives the switches 41, 42, 43, 44, 45 and 46 in accordance with an instruction from the CPU 10.

The switches 43, 44, 45 and 46 are of a two-way type having a neutral position.

One end of the piezoelectric element 2a is connected via one contact of the switch 43 to an output terminal 60a of a detection/determination circuit 60 in a detection/determination section 50. The other end of the piezoelectric element 2a is connected to an output terminal 11b of the detection/determination circuit 60 via one contact of the switch 44.

One end of the piezoelectric element 2b is connected to an output terminal 70a of the detection/determination circuit 70 in the detection/determination section 50 via one contact of the switch 44. The other end of the piezoelectric element 2b is connected to an output terminal 70b of the detection/determination circuit 70 via one contact of the switch 45.

One end of the piezoelectric element 2c is connected via one contact of the switch 45 to an output terminal 80a of a detection/determination circuit 80 in the detection/determination section 50. The other end of the piezoelectric element 2c is connected via one contact of the switch 46 to an output terminal 80b of the detection/determination circuit 80.

The detection/determination section 50 comprises the detection/determination circuits 60, 70, 80, OR circuit 51 and CPU 52.

The detection/determination circuit 60 includes a detection circuit which comprises the output terminals 60a, 60b connected to the piezoelectric element 2a of the ultrasonic vibration element 2, AC power source 61 for supplying an AC voltage to the output terminals 60a, 60b, switch 62 provided on a conduction path between the AC power source 61 and the output terminals 60a, 60b, current detector 63 provided on a conduction path between the AC power source 61 and the output terminals 60a, 60b, voltage detector 64 connected to the AC power source 61 via the switch 62, computing section for computing the impedance of the piezoelectric element 2a of the ultrasonic vibration element 2 from the detection voltage of the voltage detector 64 and detection current of the current detector 63, and switch drive circuit 67 for driving the switch 62. The detection/determination circuit 60 further comprises a determination circuit 66.

Here, the computing section 65 divides the detection voltage V of the voltage detector 64 by the electric current of the current detector 63 and finds an impedance $Z_a$ of the piezoelectric element 2a. The impedance $Z_a$ thus found is sent from the computing section 65 to the determining circuit 66.

The determining circuit 66 determines whether the piezoelectric element 2a is good or not in accordance with the impedance $Z_a$. If the determining circuit 66 determines the piezoelectric element 2a as being defective, then it generates a logic "1" signal.

The switch drive circuit 67 drives the switch 62 in accordance with an instruction from the CPU 52.

The detection/determination circuit 70 has a detection circuit which comprises the output terminals 70a, 70b connected to the piezoelectric element 2b of the ultrasonic vibration element 2, an AC power source 71 for supplying an AC voltage to the output terminal 70a, 70b, switch 72 provided on a conduction path between the AC power source 71 and the output terminals 70a, 70b, current detector 73 provided on a conduction path between the AC power source 71 and the output terminals 70a, 70b, voltage detector 74 connected to the AC power source 71 via the switch 72, computing section for computing an impedance of the piezoelectric element 2b of the ultrasonic vibration element 2 from the detection voltage of the voltage detector 74 and detection current of the current detector 73, and switch drive circuit 77 for driving the switch 72. The detection/determination circuit 70 further includes a judging circuit 76.

Here, the computing section 75 divides the detection voltage V of the voltage detector 74 by the detection current of the current detector 73 and finds the impedance $Z_b$ of the piezoelectric element 2b. The impedance $Z_b$ thus found is sent to the determining circuit 76.

The determining circuit 76 determines whether the piezoelectric element 2b is good or not in accordance with the impedance $Z_b$. If the circuit 76 determines the piezoelectric element 26 as being defective, then it generates a logic "1" signal.

The switch drive circuit 77 drives the switch 72 in accordance with an instruction from the CPU 52.

The detection/determination circuit 80 includes a detection circuit which comprises the output terminals 80a, 80b connected to the piezoelectric element 2c of the ultrasonic vibration element 2, AC power source 81 for supplying an AC voltage to the output terminals 80a, 80b, switch 82 provided on a conduction path between the AC power source 81 and the output terminals 80a, 80b, current detector 83 provided on a conduction path between the AC power source 81 and the output terminals 80a, 80b, voltage detector 84 connected to the AC power source 81 via the switch 82, computing section for computing an impedance of the piezoelectric element 2c of the ultrasonic vibration element 2 from the detection voltage of the voltage detector 84 and detection current of the current detector 83, and switch drive circuit 87 for driving the switch 82. The circuit 80 further includes a determining circuit 86.

Here, the computing section 85 divides the detection voltage V of the voltage detector 84 by the current of the current detector 83 and finds the impedance $Z_c$ of the piezoelectric element 2c. The impedance $Z_c$ thus found is sent to the determining circuit 86.

The determining circuit 86 determines whether the piezoelectric element 2c is good or not in accordance with the impedance $Z_c$. If the circuit determines the element 2c as being defective, it produces a logic "1" output signal.

The switch drive circuit 87 drives the switch 82 in response to an instruction of the CPU 52.

The output signals of the determining sections 66, 76 and 86 are input to the CPU 52 via the OR circuit 51.

The CPU 52 has a function means for controlling the drive circuit 5 and switch drive circuits 68, 78, 88 in accordance with an instruction and so on from the operation unit 19 and control function means for inhibiting the generation of ultrasonic vibrations from the ultrasonic vibration element 2 when the CPU 52 receives a logic "1" signal from the OR circuit 51.

The operation of the ultrasonic treating apparatus will be explained below with reference to FIGS. 8A and 8B.

Now suppose that a start-to-treat instruction is issued from the operation unit 19 to the CPU 52 at step W1. Then the CPU 52 imparts an instruction to the switch drive circuits 67, 77, 87, turning one contact of each of the switches 43, 44, 45, 46 ON at step W2.

That is, the piezoelectric element 2a is connected to the output terminals 60a, 60b in the impedance detection circuit 60.

The piezoelectric element 2b is connected to the output terminals 70a, 70b in the impedance detection circuit 70.

The piezoelectric element 2c is connected to the output terminals 80a, 80b of the impedance detection circuit 80.

The CPU 52 issues an instruction to the switch drive circuits 67, 77, and 87, turning the switches 62, 72, and 82 ON at step W3.

With the switch 62 ON, a voltage on the AC power source 61 appears across the output terminals 60a and 60b via the current detector 63. When the switch 72 is turned ON, a voltage on the AC power source 71 emerges across the output terminals 70a and 70b via the current detector 73. With the switch 82 ON, a voltage on the AC power source 81 appears across the output terminals 80a and 80b via the current detector 83.

A voltage on the output terminals 60a and 60b is applied to the piezoelectric element 2a via switches 43, 44. As a result, electric current I flows through the piezoelectric element 2a so that it is detected by the current detector 63. A result of detection is sent to the computing section 65.

A voltage V on the AC power source 61 is detected by the voltage detector 64 and a result of detection is sent to the computing section 65.

The computing section 65 divides the voltage V by the current I to find an impedance $Z_a$ of the piezoelectric element 2a at step W4. The impedance $Z_a$ thus found is fed to the determining circuit 66.

The determining circuit 66 ascertains whether or not the impedance $Z_a$ is within a predetermined range, that is, within a proper level $Z_{a1} \leq Z_a \leq Z_{a2}$ ($Z_{a1}$, $Z_{a2}$: the setting values) at step W5.

If the impedance $Z_a$ is found to be a proper level at step W6, then the determining circuit 66 determines that the piezoelectric element 2a is good at step W6, and produces a logic "0" output.

A voltage on the output terminals 70a and 70b is applied to the piezoelectric element 2b via the switches 44 and 45. Electric current I flows through the piezoelectric element $2b$ so that electric current I is detected by the current detector 73. A result of detection is supplied to the computing section 75.

A voltage V on the AC power source 71 is detected by the voltage detector 74 and a result of detection is sent to the computing section 75.

The computing section 75 divides the voltage V by the current I to find an impedance $Z_b$ of the piezoelectric element $2b$ at step W4. The impedance $Z_b$ thus found is fed to the determining circuit 76.

The determining circuit 76 ascertains whether or not the impedance $Z_b$ is within a predetermined range, that is, within a $Z_{b1} \leq Z_b \leq Z_{b2}$ range (the setting values $Z_{b1}$ and $Z_{b2}$) at step W5.

If the impedance $Z_b$ is found to be a proper value, the determining circuit 76 determines that the piezoelectric element $2b$ is good (step W6). At this time, the determining circuit 76 produces a logic "0" output.

A voltage on the output terminals $80a$ and $80b$ is applied to the piezoelectric element $2c$ via the switches 45 and 46. Electric current I flows through the piezoelectric element $2c$ so that it is detected by the current detector 83. A result of detection is fed to the computing section 85.

A voltage V on the AC power source 81 is detected by the voltage detector 84 and a result of detection is delivered to the computing section 85.

The computing section 85 divides the voltage V by the current I to find an impedance $Z_c$ of the piezoelectric element $2c$ (step W4). The impedance $Z_c$ thus found is delivered to the determining circuit 86.

The determining circuit 86 ascertains whether or not the impedance $Z_c$ is within a predetermined range, that is, within a $Z_{c1} \leq Z_c \leq Z_{c2}$ range (the setting values: $Z_{c1}$ and $Z_{c2}$)—step W5.

If, at this time, the impedance $Z_c$ is found to be a proper value, the determining circuit 86 determines that the piezoelectric element $2c$ is good (step W6). The determining circuit 86 produces a logic "0" output.

If all the piezoelectric elements $2a$, $2b$ and $2c$ are found to be good, then the OR circuit 51 produces a logic "0" output.

At this time, the CPU 52 displays "good" on the display unit 18 (step W7) and the switches 62, 72 and 82 are turned ON, thus stopping the operation of the detection/determination circuit 60, 70 and 80 (step W8).

The CPU 52 turns said other contacts of the switches 43, 44, 45 and 46 ON (step W9) and the switches 41 and 42 ON (step W10).

With said other contacts of the switches 43, 44, 45 and 46 ON, the piezoelectric elements $2a$, $2b$ and $2c$ are separated from the detection/determination circuits 60, 70 and 80. At the same time, the switches 41 and 42 are turned ON, connecting the piezoelectric elements $2a$, $2b$ and $2c$ to the drive circuit 5.

In that connection state, the CPU 52 operates the drive circuit 5 at step W11.

As a result, an electric power is supplied to the piezoelectric elements $2a$, $2b$ and $2c$ via the switches 41, 42, 43, 44, 45 and 46. Thus the ultrasonic vibration element 2 is driven, producing ultrasonic vibrations.

If, at the time of producing the ultrasonic vibration, a treatment termination instruction is issued at the operation unit 19 at step W12.

At this time, the CPU 52 ends the display "good" on the screen of the display unit 18 at step W13 and the operation of the drive circuit 5 is stopped at step W14. The CPU 52 turns the switches 41 and 42 OFF at step W15 and sets the switches 43, 44, 45 and 46 to the neutral position. The drive of the ultrasonic vibration element 2 is stopped.

If the impedance $Z_a$ falls within the proper range at step W5, the determination circuit 66 determines that the piezoelectric element $2a$ is not good at step W17. At this time, the determination circuit 66 produces a logic "1" output.

If the impedance $Z_b$ is found not to be within the proper range at step W5, the determination circuit 76 determines that the piezoelectric element $2b$ is not good at step W17. At this time, the determination circuit 76 produces a logic "1" output.

If the impedance $Z_c$ is found not to be within the proper range at step W5, the determination circuit 86 determines that the piezoelectric element $2c$ is not good (step W17). At this time, the determination circuit 86 produces a logic "1" output.

When one of these piezoelectric elements $2a$, $2b$ and $2c$ is found not to be good, the OR circuit 51 produces a logic "1" output.

At this time, the CPU 52 enables the display unit 18 to perform a display "not good" thereon at step W18. The switches 62, 72, 82 are turned OFF, stopping the operations of the detection/determination circuits 60, 70 and 80 (step W19). The CPU 52 sets the switches 43, 44, 45 and 46 to the neutral position (step W20) and inhibits the operation of the drive circuit 5 in spite of the instruction of the operation unit 5 (step W21).

In this case, the ultrasonic vibration element 2 is not driven and the ultrasonic vibration of the ultrasonic vibration element 2 is not produced, thus avoiding a risk of a breakage to, for example, an apparatus. It is, therefore, possible to insure an added degree of safety during the use of the apparatus.

The user can immediately know from the display "not good" that the lack of ultrasonic vibrations is caused by the defect of the ultrasonic vibration element 2. Therefore, the user can use the apparatus with added safety.

What is claimed is:

1. An ultrasonic treating apparatus comprising:
   an ultrasonic vibration element for transmitting ultrasonic vibrations to a region of interest of a subject;
   drive circuit means for supplying a driving electric power to said ultrasonic vibration element;
   impedance detection means for supplying a current to said ultrasonic vibration element independent of said driving electric power, and when said driving electric power is not supplied, thereby detecting an impedance of said ultrasonic vibration element;
   determining means for determining whether said ultrasonic vibration element is good or not in accordance with the impedance which is detected by said impedance detection means; and
   control means for inhibiting operation of said drive circuit means when said determining means determines said ultrasonic vibration element as not being good, thereby stopping the driving of said ultrasonic vibration element and preventing the ultrasonic vibration element from breaking down.

2. The apparatus according to claim 1, further comprising an operation unit coupled to said drive circuit means for instructing a start and an end of the ultrasonic vibrations generated by said ultrasonic vibration element.

3. The apparatus according to claim 2, wherein said impedance detection means includes:

means responsive to said operation unit instructing a start of ultrasonic vibrations, for starting detecting of an impedance; and means responsive to an end of a determination by said determining means, for stopping detection of an impedance.

4. The apparatus according to claim 1, wherein said impedance detection means comprises an output terminal to which said ultrasonic vibration element is connected, an AC power source for applying an AC voltage to said output terminal, a switch provided on a conduction path which is located between the AC power source and the output terminal, a current detector provided on a conduction path between the AC power source and said output terminal, a voltage detector connected to the AC power source via said switch and a computing section for computing the impedance of said ultrasonic vibration element from the detection voltage of the voltage detector and detection current of said current detector, said impedance detection means being operated, by the turning on of said switch, to detect the impedance of the ultrasonic vibration element.

5. The apparatus according to claim 4, wherein said computing section includes means for dividing said detection voltage of said voltage detector by said electric current of said current detector to find an impedance of said ultrasonic vibration element.

6. The apparatus according to claim 1, wherein said determining means includes means for determining said ultrasonic vibration element as being good when said impedance which is detected by said impedance detection means is within a predetermined range and as not being good when said impedance is not within said predetermined range.

7. The apparatus according to claim 1, further comprising a display unit connected to said determining means to display a result of determination by said determining means.

8. The apparatus according to claim 1, further comprising an ultrasonic transmitting unit for transmitting ultrasonic vibrations which are generated from said ultrasonic vibration element to said region of interest.

9. An ultrasonic treating apparatus comprising:
an ultrasonic vibration element for transmitting ultrasonic vibrations to a region of interest of a subject;
drive circuit means for supplying electric power to drive the ultrasonic vibration element;
burst drive control means for operating said drive circuit means in an ON-OFF fashion;
impedance detection means for supplying a current to said ultrasonic vibration element independent of said electric power supplied by said drive circuit means, and when said electric power is not supplied by said drive circuit means, and for detecting an impedance of said ultrasonic vibration element;
determining means, responsive to said impedance detection means, for determining whether said ultrasonic vibration element is good or not; and
control means for inhibiting operation of said drive circuit means when said determining means determines the ultrasonic vibration element as not being good, thereby stopping the driving of said ultrasonic vibration element and preventing breaking down of the ultrasonic vibration element.

10. The apparatus according to claim 9, further comprising a switching circuit for connecting said ultrasonic vibration element to said drive circuit means when the drive circuit means is turned on and to said impedance detection means when the drive circuit means is turned off.

11. The apparatus according to claim 9, further comprising a display unit connected to said determining means to display a result of determination by said determining means.

12. The apparatus according to claim 9, further comprising an ultrasonic wave transmitting unit for transmitting ultrasonic vibrations which are generated from said ultrasonic vibration element to said region of interest.

13. An ultrasonic treating apparatus comprising:
an ultrasonic vibration element including an array of joined piezoelectric elements to form one body structure and adapted to transmit ultrasonic vibrations to a region of interest;
drive circuit means for supplying a driving electric power to the ultrasonic vibration element;
impedance detection means for supplying a current to each piezoelectric element, and for detecting an impedance of each piezoelectric element independent of the supply of electric power by said drive circuit means and when said electric power is not supplied by said drive circuit means;
determining means for determining whether each piezoelectric element is good or not in accordance with an impedance value which is detected by said impedance detection means; and
control means for inhibiting an operation of said drive circuit means to prevent supply of said electric power when a piezoelectric element is determined as not being good.

14. The apparatus according to claim 13, further comprising an operation unit coupled to said drive circuit means for instructing a start and an end of the ultrasonic vibrations generated by said ultrasonic vibration element.

15. The apparatus according to claim 14, wherein said impedance detection means includes:
means responsive to said operation unit instructing a start of ultrasonic vibrations, for starting detecting of an impedance; and
means responsive to an end of a determination by said determining means, for stopping detection of an impedance.

16. The apparatus according to claim 13, wherein said impedance detection means is comprised of a plurality of impedance detection circuits each corresponding to one of the piezoelectric elements in said ultrasonic vibration element.

17. The apparatus according to claim 13, wherein said determining means comprises a plurality of determining circuits each corresponding to one of the piezoelectric elements in said ultrasonic vibration element.

18. The apparatus according to claim 17, wherein said control means inhibits an operation of said drive circuit means when a not good state is determined by any one of said plurality of determining circuits.

* * * * *